(12) United States Patent
Pastore et al.

(10) Patent No.: US 7,689,286 B2
(45) Date of Patent: Mar. 30, 2010

(54) MYOCARDIUM CONDITIONING USING MYOCARDIAL AND PARASYMPATHETIC STIMULATION

(75) Inventors: Joseph M. Pastore, Woodbury, MN (US); Tamara Colette Baynham, Blaine, MN (US); Andrew P. Kramer, Stillwater, MN (US); Julio C. Spinelli, Shoreview, MN (US); Jeffrey Ross, Roseville, MN (US); Rodney W. Salo, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 327 days.

(21) Appl. No.: 11/381,211

(22) Filed: May 2, 2006

(65) Prior Publication Data
US 2007/0260284 A1 Nov. 8, 2007

(51) Int. Cl.
*A61N 1/362* (2006.01)
(52) U.S. Cl. .......................... 607/50; 607/9
(58) Field of Classification Search .............. 607/2, 607/4, 5, 9, 11, 14, 117; 600/509, 512, 515, 600/517
See application file for complete search history.

(56) References Cited

U.S. PATENT DOCUMENTS

| | | | | |
|---|---|---|---|---|
| 5,199,428 A | * | 4/1993 | Obel et al. | 607/44 |
| 5,203,326 A | * | 4/1993 | Collins | 607/4 |
| 5,330,507 A | * | 7/1994 | Schwartz | 607/14 |
| 5,522,854 A | * | 6/1996 | Ideker et al. | 607/6 |
| 5,578,061 A | * | 11/1996 | Stroetmann et al. | 607/4 |
| 5,658,318 A | * | 8/1997 | Stroetmann et al. | 607/6 |
| 6,006,134 A | * | 12/1999 | Hill et al. | 607/9 |
| 6,016,443 A | * | 1/2000 | Ekwall et al. | 600/519 |
| 6,108,577 A | | 8/2000 | Benser | |
| 6,233,486 B1 | * | 5/2001 | Ekwall et al. | 607/17 |
| 7,215,992 B2 | | 5/2007 | Stahmann et al. | |
| 7,295,874 B2 | | 11/2007 | Prinzen et al. | |
| 7,299,086 B2 | | 11/2007 | McCabe et al. | |
| 2003/0060854 A1 | | 3/2003 | Zhu | |
| 2003/0181951 A1 | * | 9/2003 | Cates | 607/9 |

(Continued)

FOREIGN PATENT DOCUMENTS

WO WO-00/57781 A1 10/2000

(Continued)

OTHER PUBLICATIONS

"Diagram—Akt Pathway", [online]. [archived on Feb. 6, 2005]. Retrieved from the Internet: <URL: http://web.archive.org/web/20050206204500/http://www.upstate.com/img/pathways/akt_pkb.jpg> (2005), 1 pg.

(Continued)

*Primary Examiner*—Carl H Layno
*Assistant Examiner*—Roland Dinga
(74) *Attorney, Agent, or Firm*—Schwegman, Lundberg & Woessner, P.A.

(57) ABSTRACT

Various system embodiments comprise a neural stimulator, a pulse generator, and a controller. The neural stimulator is adapted to generate a neural stimulation signal. The pulse generator is adapted to generate a pacing signal to provide myocardium pacing. The controller is adapted to control the neural stimulator and the pulse generator to provide a cardioprotective conditioning therapy. The conditioning therapy includes neural stimulation to elicit a parasympathetic response and myocardium pacing. Other aspects and embodiments are provided herein.

30 Claims, 12 Drawing Sheets

U.S. PATENT DOCUMENTS

| | | | |
|---|---|---|---|
| 2004/0015081 A1* | 1/2004 | Kramer et al. | 600/439 |
| 2004/0049117 A1* | 3/2004 | Ideker et al. | 600/510 |
| 2004/0133247 A1* | 7/2004 | Stahmann et al. | 607/17 |
| 2004/0193231 A1* | 9/2004 | David et al. | 607/48 |
| 2004/0199210 A1* | 10/2004 | Shelchuk | 607/17 |
| 2005/0283197 A1 | 12/2005 | Daum et al. | |
| 2006/0116593 A1 | 6/2006 | Zhang et al. | |
| 2006/0241704 A1 | 10/2006 | Shuros et al. | |
| 2006/0253156 A1 | 11/2006 | Pastore et al. | |
| 2006/0259087 A1 | 11/2006 | Baynham et al. | |
| 2007/0043393 A1 | 2/2007 | Brockway et al. | |

FOREIGN PATENT DOCUMENTS

| | | |
|---|---|---|
| WO | WO-2005/113066 A1 | 12/2005 |
| WO | WO-2007/130774 A2 | 11/2007 |

OTHER PUBLICATIONS

"PCT Application No. PCT/US2007/066383, International Search Report mailed Dec. 6, 2007", 3 pgs.

"PCT Application No. PCT/US2007/066383, Written Opinion mailed Dec. 6, 2007", 6 pgs.

Darling, C. E., et al., "'Postconditioning' via Stuttering Reperfusion Limits Myocardial Infarct Size in Rabbit Hearts: Role of ERK 1/2.", *American Journal of Physiology—Heart and Circulatory Physiology*, 289(4), (2005), 1618-1626.

Dzwonczyk, R., et al., "Myocardial Electrical Impedance Responds to Ischemia and Reperfusion in Humans", *IEEE Transactions on Biomedical Engineering*, 51(12), (2004), 2206-2209.

Hausenloy, D. J., et al., "Ischemic Preconditioning Protects by Activating Prosurvival Kinases at Reperfusion.", *American Journal of Physiology—Heart And Circulatory Physiology*, 288(2), (2005), H971-H976.

Krieg, T., et al., "Acetylcholine and Bradykinin Trigger Preconditioning in the Heart Through a Pathway that Includes Akt and NOS.", American Journal of Physiology—Heart and Circulatory Physiology, 28(6), (2004), H2606-H2611.

Morris, S. D., et al., "Angiotensin-Converting Enzyme Inhibitors Potentiate Preconditioning Through Bradykinin $B_2$ Receptor Activation in Human Heart.", *Journal of the American College of Cardiology*, 29(7), (Jun. 1997), 1599-606.

Tsang, A., et al., "Postconditioning: A form of "Modified Reperfusion" Protects the Myocardium by Activating the Phosphatidylinositol 3-Kinase-Akt Pathway", *Circulation Research*, 95(3), Epub Jul. 8, 2004.,(Aug. 6, 2004),230-2.

"European Application Serial No. 07797222.2, Communication mailed Feb. 18, 2009", 2 pgs.

* cited by examiner

MYOCARDIUM CONDITIONING USING MYOCARDIAL AND PARASYMPATHETIC STIMULATION

TECHNICAL FIELD

This application relates generally to the treatment of heart disease and, more particularly, to systems, devices and methods to provide myocardial conditioning using myocardial and parasympathetic stimulation.

BACKGROUND

The heart is the center of a person's circulatory system. The left portions of the heart draw oxygenated blood from the lungs and pump it to the organs of the body to provide the organs with their metabolic needs for oxygen. The right portions of the heart draw deoxygenated blood from the body organs and pump it to the lungs where the blood gets oxygenated. Contractions of the myocardium provide these pumping functions. In a normal heart, the sinoatrial node, the heart's natural pacemaker, generates electrical impulses that propagate through an electrical conduction system to various regions of the heart to excite the myocardial tissues of these regions. Coordinated delays in the propagations of the electrical impulses in a normal electrical conduction system causes the various portions of the heart to contract in synchrony, which efficiently pumps the blood. Blocked or abnormal electrical conduction or deteriorated myocardial tissue causes dysynchronous contraction of the heart, resulting in poor hemodynamic performance, including a diminished blood supply to the heart and the rest of the body. Heart failure occurs when the heart fails to pump enough blood to meet the body's metabolic needs.

An occlusion of a blood vessel such as a coronary artery interrupts blood supply to the myocardium, which deprives the myocardium is deprived of adequate oxygen and metabolite removal, and results in cardiac ischemia. Myocardial infarction (MI) is the necrosis of portions of the myocardial tissue which results from cardiac ischemia. The necrotic tissue, known as infarcted tissue, loses the contractile properties of normal, healthy myocardial tissue. The overall contractility of the myocardium is weakened, resulting in an impaired hemodynamic performance. Following an MI, cardiac remodeling starts with expansion of the region of infarcted tissue and progresses to a chronic, global expansion in the size and change in the shape of the entire left ventricle. The consequences include a further impaired hemodynamic performance and a significantly increased risk of developing heart failure, as well as a risk of suffering recurrent MI.

Therefore, there is a need to protect the myocardium from injuries associated with ischemic events, including MI.

SUMMARY

Various aspects of the present subject matter relate to a system. Various system embodiments comprise a neural stimulator, a pulse generator, and a controller. The neural stimulator is adapted to generate a neural stimulation signal. The pulse generator is adapted to generate a pacing signal to provide myocardium pacing. The controller is adapted to control the neural stimulator and the pulse generator to provide a cardioprotective conditioning therapy. The conditioning therapy includes neural stimulation to elicit a parasympathetic response and myocardium pacing.

Various aspects of the present subject matter relate to a method. According to various embodiments of the method, cardioprotective therapy is provided to treat heart disease. The cardioprotective therapy includes cardioprotective pacing therapy, and cardioprotective neural stimulation therapy to elicit a parasympathetic response.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Various embodiments provide myocardial and neural stimulation to effect prophylactic and/or therapeutic cardioprotection. The neural stimulation elicits a parasympathetic response and can include stimulation of parasympathetic nerve traffic (e.g. vagal stimulation) and/or inhibition of sympathetic nerve activity. An ischemia detection system can be used to trigger cardioprotective therapy after ischemia has been detected.

Akt-Mediated Pathway

Various animal models have demonstrated that periodic pacing prior to an ischemic insult results in cardioprotective effects such as decreased infarct size as well as decreased incidences of arrhythmias. The delivery of intermittent ventricular pacing has been proposed to elicit these cardioprotective effects. One potential cellular mechanism of action of cardioprotection is modulation of the Akt-mediated pathway. This Akt-mediated pathway has been implicated in both prophylactic preconditioning (Hausenloy et al., Ischemic Preconditioning Protects By Activating Prosurvival Kinases At Reperfusion, *Am J Physiol Heart Circ Physiol*, 288: H971-76 (2005)) and therapeutic postconditioning (Tsang et al., Postconditioning: A Form Of "Modified Reperfusion" Protects The Myocardium By Activating The Phosphatidylinositol 3-Kinase-Akt Pathway, *Circ Res*, 95:230-32 (2004)) in various animal models.

Figure 1:
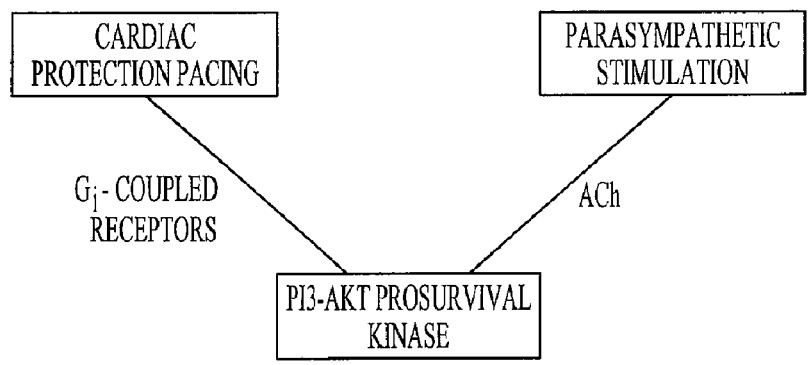
FIG. 1 illustrates therapies to affect a PI3-Akt prosurvival kinase, according to various embodiments of the present subject matter.

FIG. 1 illustrates therapies to affect a PI3-Akt prosurvival kinase, according to various embodiments of the present subject matter. A kinase is an enzyme that catalyzes the conversion of a proenzyme to an active enzyme. A result of affecting the PI3-Akt prosurvival kinase is to reduce apoptosis (programmed cell death). As illustrated in the figure, cardiac protective pacing activates the PI3-Akt prosurvival kinase via $G_i$-coupled receptors (Krieg et al., Acetylcholine And Bradykinin Trigger Preconditioning In The Heart Through A Pathway That Includes Akt and NOS, *Am J Physiol Heart Circ Physiol*, 287:H2606-11 (2005)). As also illustrated in FIG. 1, the present subject matter also accesses the Akt-mediated pathway using parasympathetic neural stimulation via Ach (acetylcholine), one of the predominant transmitters in the autonomic nervous system. Ach is a parasympathetic neurotransmitter liberated from preganglionic and postganglionic endings of parasympathetic fibers, whereupon it acts as a transmitter on the effector organ. Ach causes cardiac inhibition, vasodilation, gastrointestinal peristalsis, and other parasympathetic effects. Thus, the Akt-mediated pathway is also affected by vagal nerve stimulation (VNS), or more generally stimulation of a parasympathetic neural target that innervates the myocardium.

The present subject matter protects the heart from injuries associated with ischemic events, including MI. This document describes a device which combines periodic myocardium pacing and parasympathetic stimulation to deliver cardioprotective therapy. One device embodiment, for example, delivers pacing therapy at regular (e.g. 5 minutes of pacing every hour) or random intervals and delivers parasympathetic stimulation. The two therapies may be delivered simultaneously, sequentially, or on different time schedules. The neural stimulation is delivered to a parasympathetic neural target that innervates the myocardium, such as a vagus nerve, a branch of a vagus nerve, or a cardiac fat pad. Various embodiments selectively stimulate a desired neural pathway within the vagus nerve to produce Ach from the endings of parasympathetic fibers at desired portions the myocardium. Parasympathetic stimulation is applied at a frequency, amplitude, and periodicity (e.g. 300 ms pulses at 1-2 mA for 10 seconds every minute) selected to stimulate the parasympathetic neural target. In various embodiments, the therapies are delivered through different leads, and various embodiments deliver the therapies using either the same or independent pulse generators.

The combination of pacing and parasympathetic stimulation may provide an additive effect as illustrated with other preconditioning triggers (Morris et al, Angiotensin-Converting Enzyme Inhibitors Potentiate Preconditioning Through Bradykinin B2 Receptor Activation In Human Heart, *J Am Coll Cardiol.*, 29: 1599-1606 (1997)). The device may be coupled with an ischemia detection system to control the delivery of therapy after the detection of an ischemic event.

Since the Akt-mediated pathway is also implicated in protection from ischemia/reperfusion, both myocardial and vagal stimulation may provide protection after the ischemic event. The device may also be used at the time of scheduled revascularization procedures to protect the myocardium from ischemia/reperfusion injury as well as to provide preconditioning for possible ischemic events as a result of the revascularization therapy. The present subject matter may benefit any patient at high-risk of a first or recurrent myocardial infarction, and may be included in a device designed to apply therapy for angina, and the pre/post conditioning therapy may be controlled based upon sensing of cardiac ischemia.

Myocardial Conditioning

The myocardium conditioning therapy with myocardial pacing and parasympathetic stimulation can be provided according to a variety of protocols. Examples of some of these protocols are illustrated here.

Figure 2A:
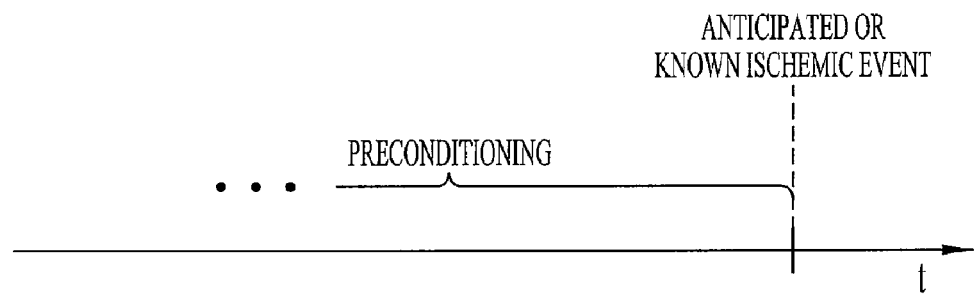
FIGS. 2A-2B illustrate myocardium preconditioning and myocardium postconditioning, respectively, according to various embodiments of the present subject matter.
Figure 2B:
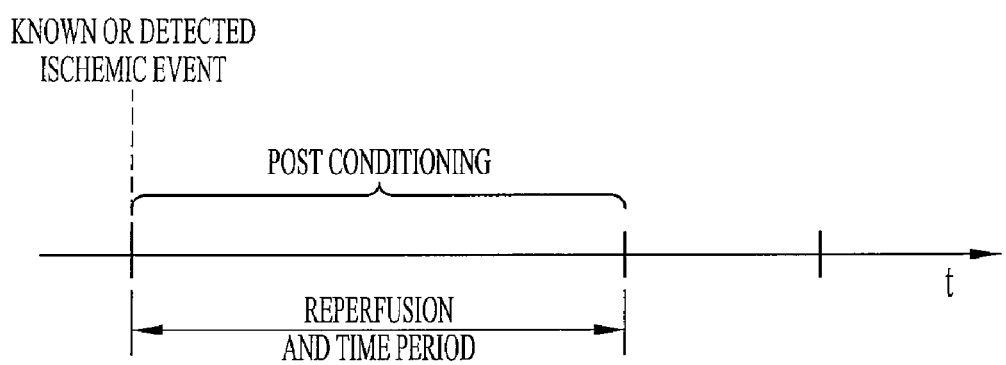

FIGS. 2A-2B illustrate myocardium preconditioning and myocardium postconditioning, respectively, according to various embodiments of the present subject matter. FIG. 2A illustrates a time line with an anticipated or known ischemic event. Preconditioning of the myocardium occurs as a prophylactic therapy in preparation for the known or anticipated ischemic event. According to the present subject matter, the preconditioning includes myocardial pacing and parasympathetic stimulation. For example, the myocardium can be preconditioned in anticipation for surgery, or can be preconditioned based on observed or detected events that indicate an increased probability of an upcoming ischemic event. Examples of such events include a previous myocardial infarction and angina. FIG. 2B illustrates a time line with a known or detected ischemic event. Postconditioning of the myocardium occurs as a therapeutic therapy to reduce the size of any infarct area caused by the ischemic event. According to the present subject matter, the postconditioning includes myocardial pacing and parasympathetic stimulation. For example, the postconditioning therapy can be triggered based on commands received from a patient or physician after observing a myocardial infarction, or a physician can deliver postconditioning therapy after a surgical procedure for which the heart was stopped. In an embodiment, the device detects an ischemic event, and automatically delivers the postconditioning therapy. The postconditioning therapy can occur during the time of reperfusion, for a time after reperfusion, or during and for a time after reperfusion.

Figure 3A:
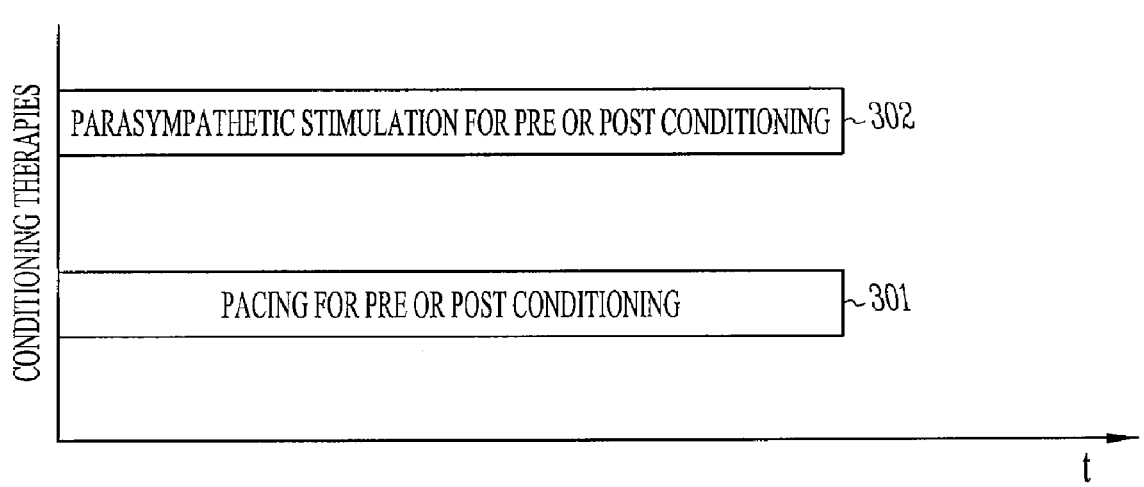
FIGS. 3A-3B illustrate simultaneous and sequential, respectively, delivery of parasympathetic stimulation therapy and pacing therapy, according to various embodiments of the present subject matter.
Figure 3B:
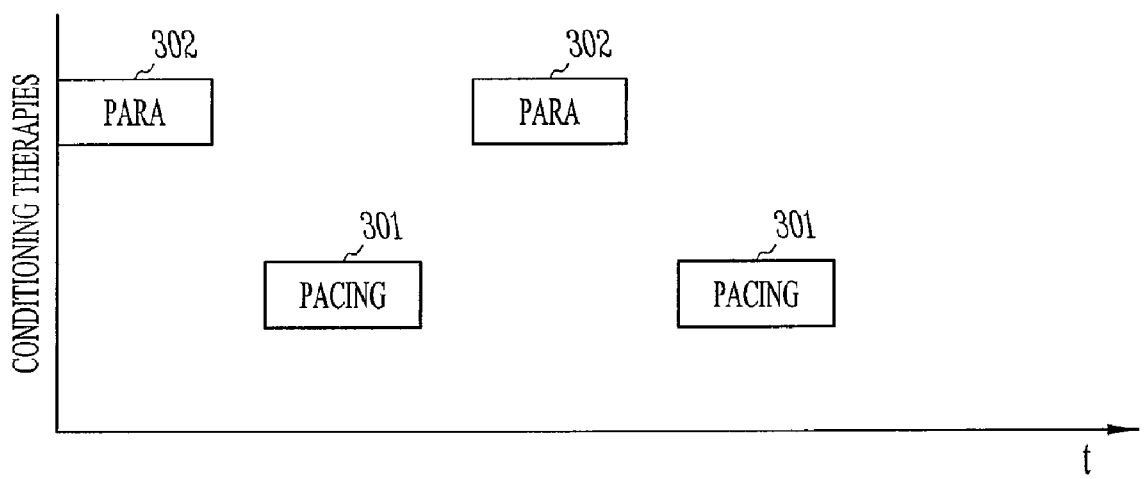

FIGS. 3A-3B illustrate simultaneous and sequential, respectively, delivery of parasympathetic stimulation therapy and pacing therapy, according to various embodiments of the present subject matter. FIG. 3A illustrates a time line, upon which myocardial pacing 301 to condition the myocardium occurs at the same time or independently of the parasympathetic stimulation 302 for conditioning the myocardium. The figure illustrates both therapies starting and ending at the same time. Other start and end times are within the scope of the present subject matter. FIG. 3B illustrates a time line, upon which the parasympathetic stimulation 302 and myocardial pacing 301 occurs at a staggered or sequential times, such that the parasympathetic stimulation does not occur at the same time as the myocardial pacing. The figure illustrates parasympathetic stimulation, and then myocardial pacing, and then parasympathetic stimulation, and then pacing stimulation. Other orders are within the scope of the present subject matter.

Figure 4A:
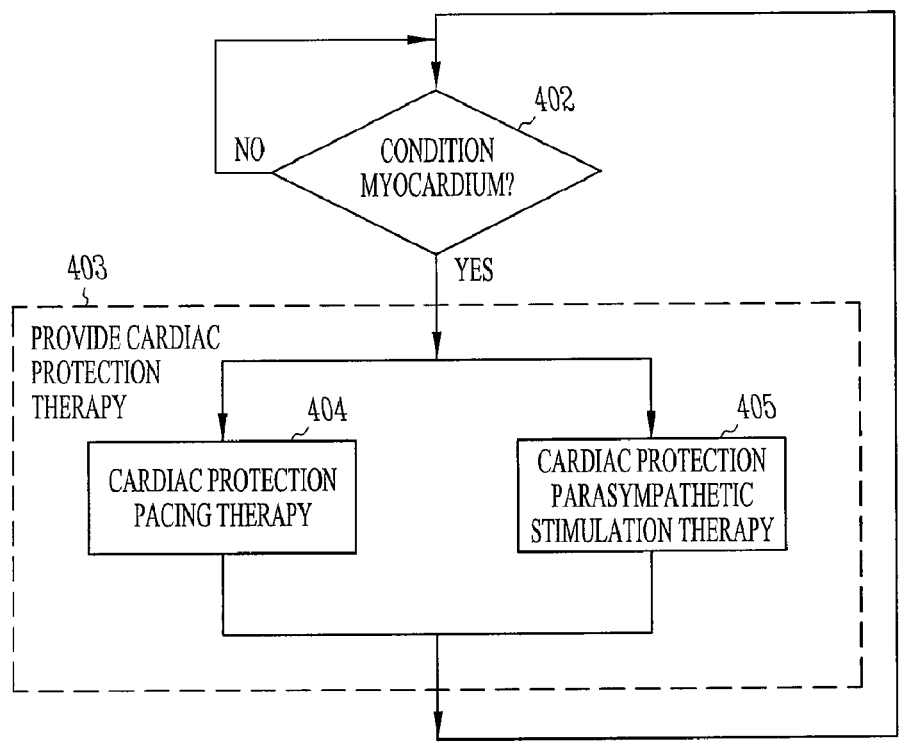
FIGS. 4A-4C illustrate methods for providing pacing and parasympathetic stimulation therapies to condition myocardium, according to various embodiments of the present subject matter.
Figure 4B:
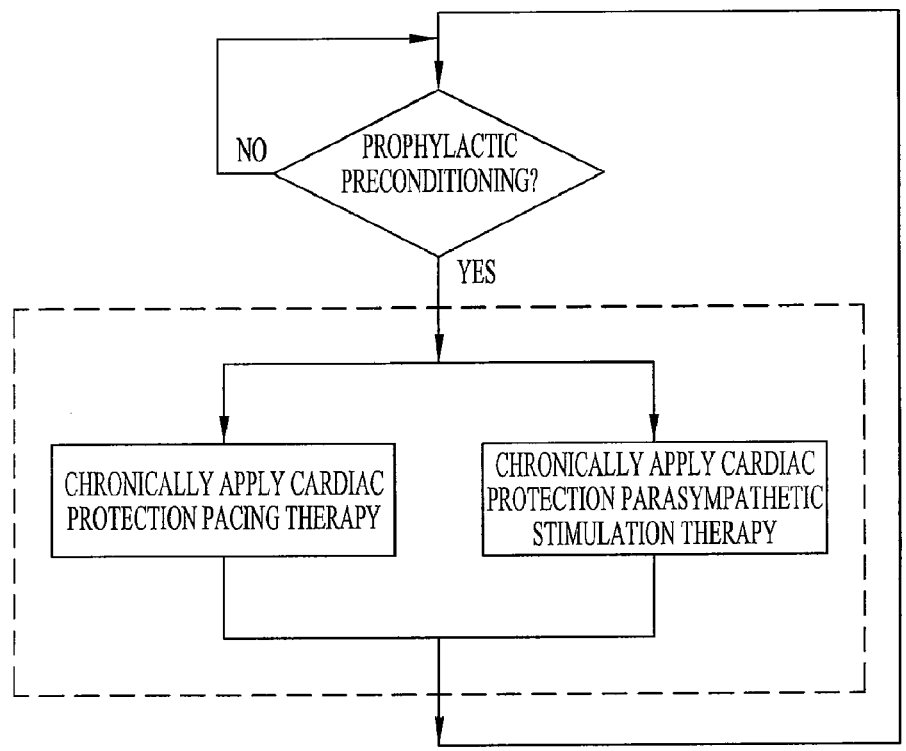
Figure 4C:
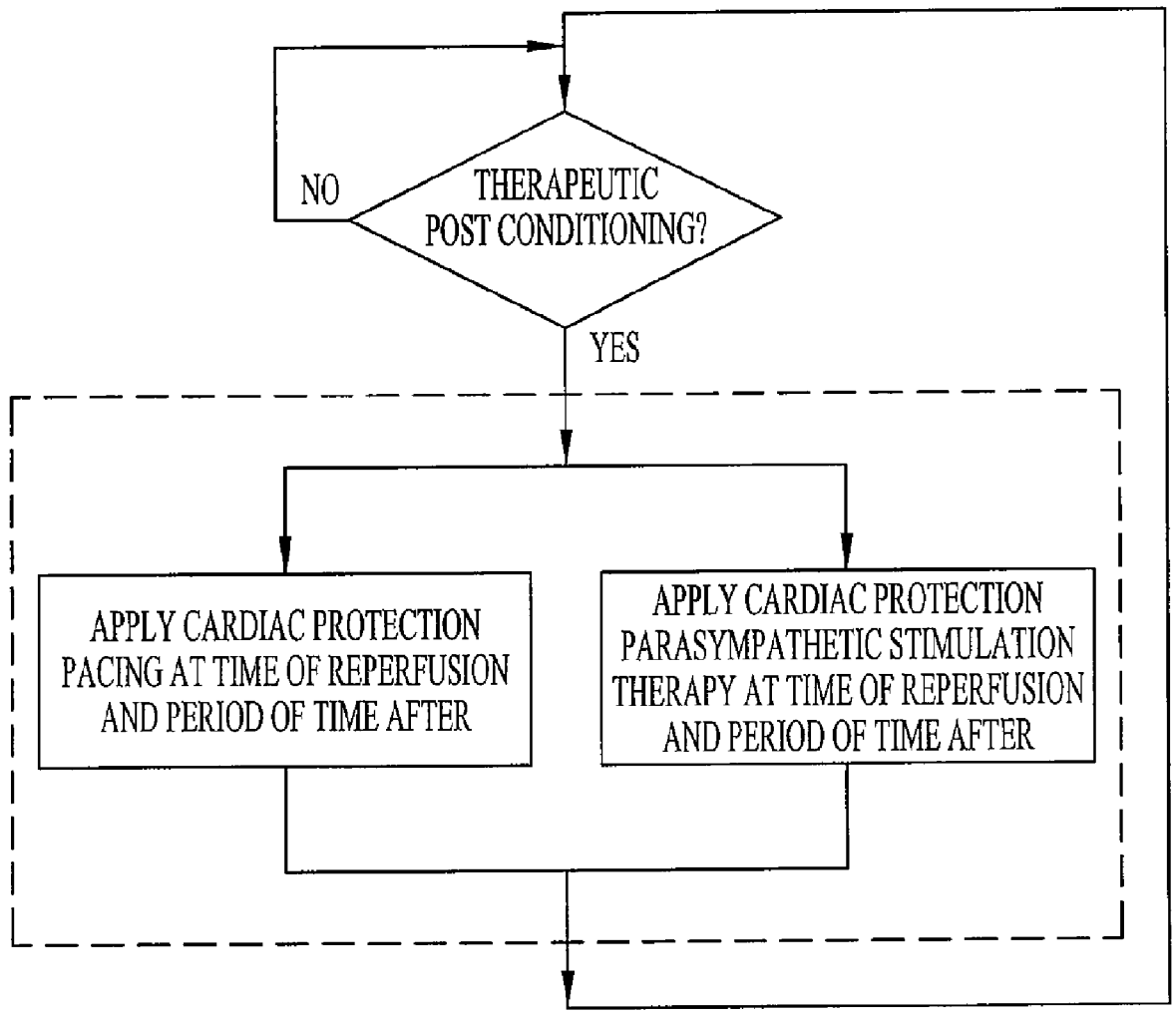

FIGS. 4A-4C illustrate methods for providing pacing and parasympathetic stimulation therapies to condition myocardium, according to various embodiments of the present subject matter. As illustrated in FIG. 4A, it is determined at 402 whether to implement a therapy to condition myocardium. Once it is determined to condition myocardium, the process proceeds to provide a cardiac protection therapy at 403. The therapy 403 includes cardiac protection pacing therapy, illustrated at 404, and cardiac protection parasympathetic stimulation therapy, illustrated at 405. The therapies 404 and 405 can be performed independently, or can be controlled to provide an integrated therapy. The therapies 404 and 405 also can be timed to avoid simultaneous therapy applications, or can be timed to allow simultaneous therapy applications.

FIG. 4B illustrates a method for providing pacing and parasympathetic stimulation therapies to provide prophylactic preconditioning therapy of the myocardium. Reasons for initiating a prophylactic preconditioning therapy include preparation for a surgical procedure, or an expected ischemic event due to sensed or known risk factors. As illustrated in FIG. 4B, both the cardiac protection pacing therapy and the cardiac protection parasympathetic stimulation therapy are chronically applied because of sensed or known risk factors, according to various embodiments.

FIG. 4C illustrates a method for providing pacing and parasympathetic stimulation therapies to provide therapeutic postconditioning therapy of the myocardium. Reasons for initiating a therapeutic therapy include part of a surgical process for repurfusing the myocardium, a sensed or observed myocardial infarction, or any other sensed ischemic event. As illustrated in FIG. 4C, both the cardiac protection pacing and the cardiac protection parasympathethic stimulation are applied during at least a portion of reperfusion and for a period of time after the reperfusion of the myocardium, according to various embodiments. Various embodiments adjust the timing of the postconditioning therapy to occur only after reperfusion or to occur only during reperfusion.

Device Examples

Figure 5:
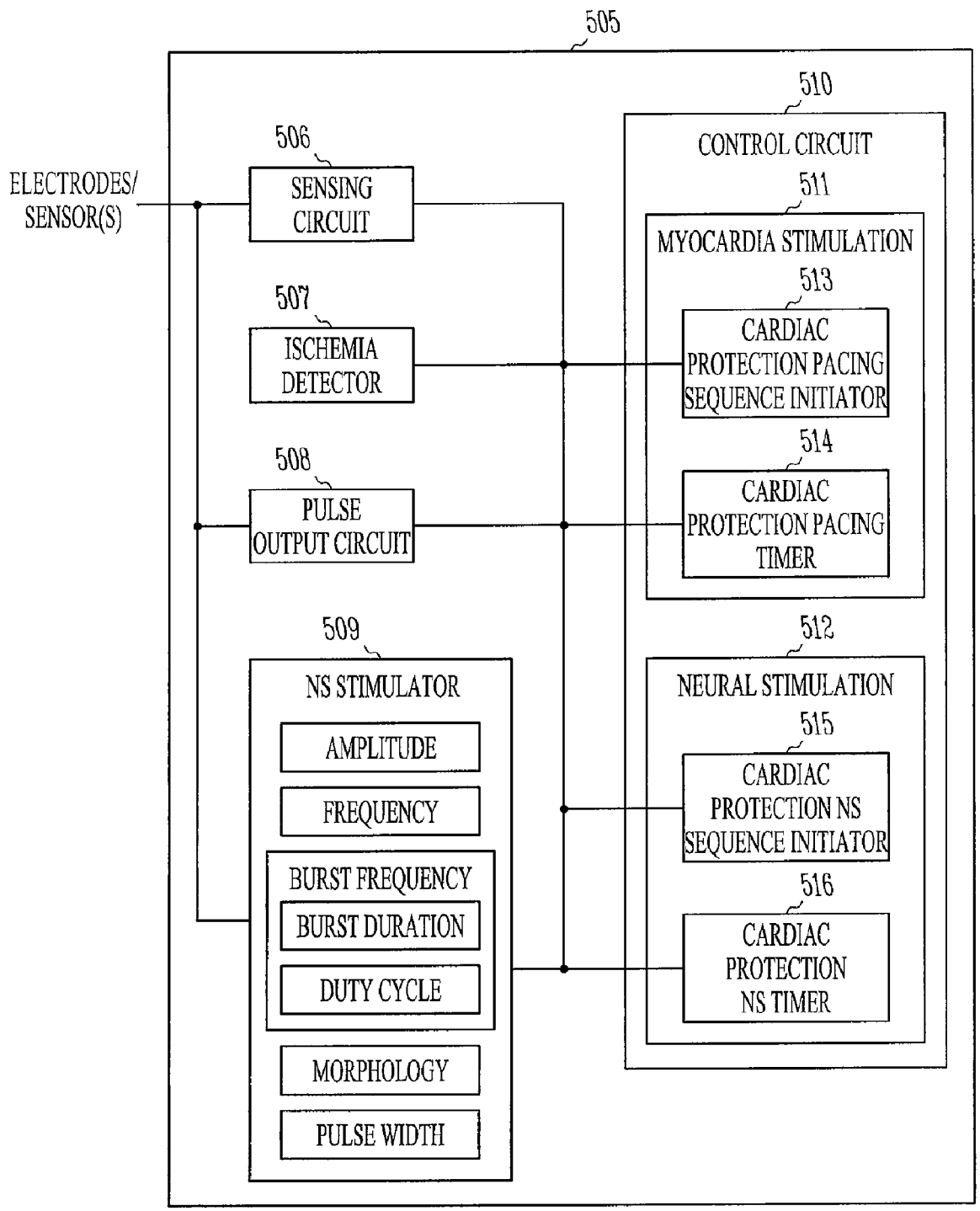
FIG. 5 illustrates a device embodiment for providing pacing and parasympathetic stimulation therapies to condition myocardium, according to various embodiments of the present subject matter.

FIG. 5 illustrates a device embodiment for providing pacing and parasympathetic stimulation therapies to condition myocardium, according to various embodiments of the present subject matter. The illustrated device 505 includes a sensing circuit 506, an ischemia detector 507, a pulse output circuit 508, a neural stimulator 509, and a control circuit 510. Sensing circuit 506 senses one or more signals using a number of electrodes and/or one or more sensors. The one or more signals are indicative of ischemic events. Ischemia detector 507 detects the ischemic events from the signals. Pulse output circuit 508 delivers myocardial pacing pulses to the heart, and neural stimulator 509 provides neural stimulation to a parasympathetic neural network that innervates the heart, such as a vagus nerve, a branch of the vagus nerve, or a cardiac fat pad. Control circuit 510 controls the delivery of the pacing pulses and neural stimulation based on the one or more sensed signals and/or in response to the detection of each ischemic event. In various embodiments, the device 505 is substantially contained in an implantable housing of implantable medical device.

The control circuit 510 includes a myocardial stimulation module 511 and a neural stimulation module 512. The myocardial stimulation module 511 includes a cardiac protection pacing sequence initiator 513 and a cardiac protection pacing timer 514. Cardiac protection pacing sequence initiator 513 initiates one or more cardiac protection pacing sequences in response to the detection of each ischemic event. The one or more cardiac protection pacing sequences each include alternating pacing and non-pacing periods. The pacing periods each have a pacing duration during which a plurality of pacing pulse is delivered. The non-pacing periods each have a non-pacing duration during which no pacing pulse is delivered. Once a cardiac protection pacing sequence is initiated, cardiac protection pacing timer 514 times that sequence. For example, various embodiments provide pacing for 5 minutes of every hour. Various events can also be sensed and used as an input to time the stimulation at desired times. Examples of sensors to detect such events include activity sensors. The neural stimulation module 512 includes a cardiac protection neural stimulation sequence initiator 515 and a cardiac protection neural stimulation timer 516. Cardiac protection neural stimulation sequence initiator 515 initiates one or more cardiac protection neural stimulation sequences in response to the detection of each ischemic event. The one or more cardiac protection neural stimulation sequences each include alternating stimulation and non-stimulation periods. The stimulation periods each have a duration during which neural stimulation is delivered to a parasympathetic target. The non-stimulation periods each have a non-stimulation duration during which no neural stimulation is delivered. Once a cardiac protection neural stimulation sequence is initiated, cardiac protection neural stimulation timer 516 times that sequence. For example, various embodiments provide neural stimulation (e.g. 300 ms pulses at 1-2 mA) for 10 seconds every minute. According to various embodiments, the neural stimulator circuitry 509 includes modules to set or adjust any one or any combination of two or more of the following pulse features: the amplitude of the stimulation pulse, the frequency of the stimulation pulse, the burst frequency of the pulse, the wave morphology of the pulse, and the pulse width. The illustrated burst frequency pulse feature includes burst duration and duty cycle, which can be adjusted as part of a burst frequency pulse feature or can be adjusted separately without reference to a steady burst frequency.

The neural stimulator may use electrodes to delivery electrical stimulation to a neural target. These neural electrodes can be on the same lead or on different leads as the cardiac pacing electrodes, depending on the locations of the desired parasympathetic neural target. Some embodiments use other techniques to deliver other energy to stimulate the neural target. For example, some embodiment use transducers to produce ultrasound or light energy waves to stimulate the neural target.

Figure 6:
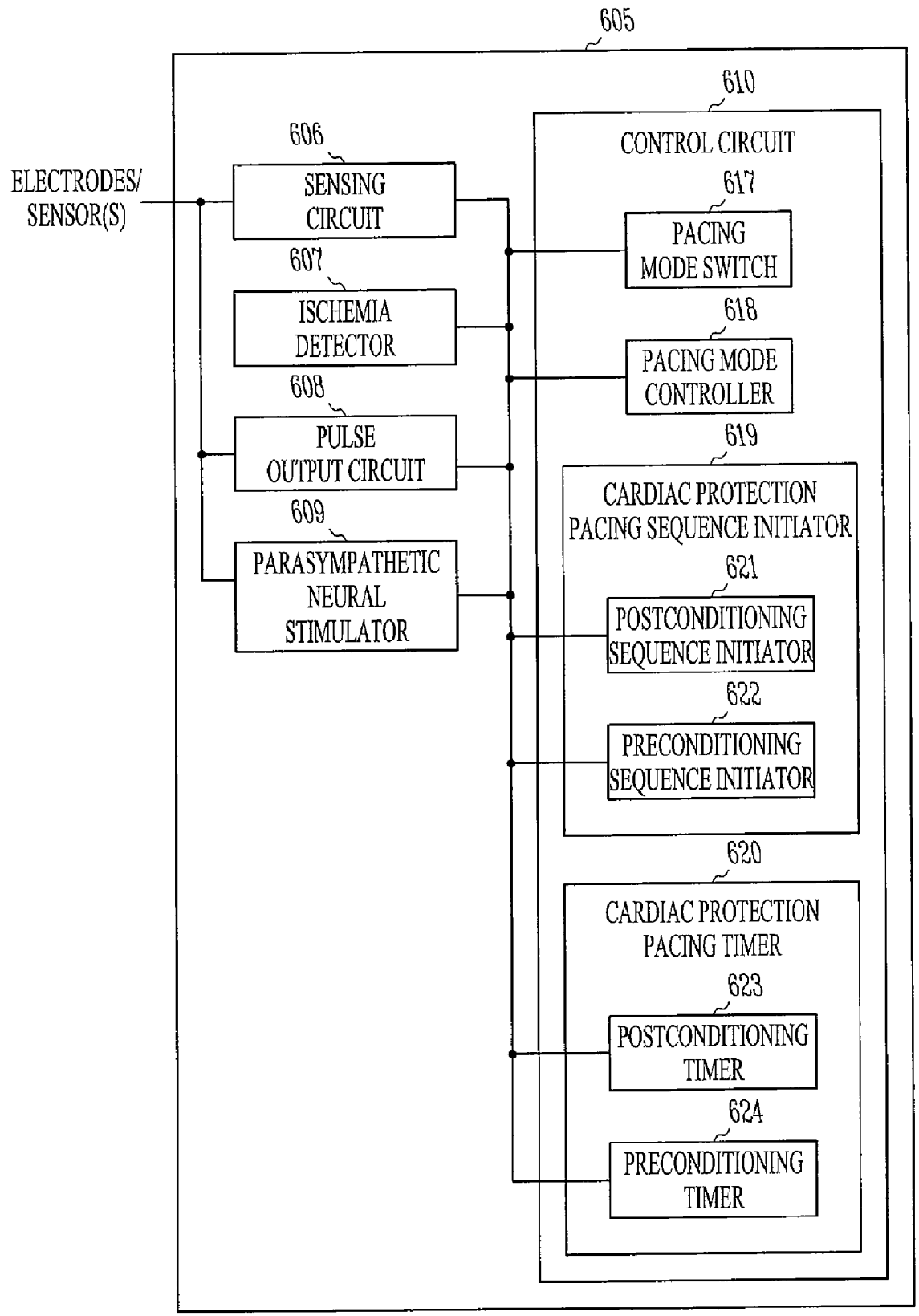
FIG. 6 illustrates a device embodiment for providing pacing and parasympathetic stimulation to condition myocardium as part of preconditioning and postconditioning therapies, according to various embodiments of the present subject matter.

FIG. 6 illustrates a device embodiment for providing pacing and parasympathetic stimulation to condition myocardium as part of preconditioning and postconditioning therapies, according to various embodiments of the present subject matter. The illustrated device 605 includes sensing circuit 606, ischemia detector 607, pulse output circuit 608, neural stimulator 609, and a control circuit 610. Sensing circuit 606 senses the one or more signals indicative of the ischemic events. Ischemia detector 607 detects the ischemic events from the one or more signals. Pulse output circuit 608 delivers the pacing pulses to heart. Control circuit 610 controls the delivery of the pacing pulses and neural stimulation based on the one or more sensed signals and/or in response to the detection of each ischemic event. In various embodiments, the device 605 is substantially contained in an implantable housing of implantable medical device.

Ischemia detector 607 includes an ischemia analyzer running an automatic ischemia detection algorithm to detect the ischemic event from the one or more signals. In one embodiment, ischemia detector 607 produces an ischemia alert signal indicative of the detection of each ischemic event. The ischemia signal is transmitted to an external system for producing an alarm signal and/or a warning message for the patient and/or a physician or other caregiver.

In one embodiment, ischemia detector 607 detects the ischemic events from one or more cardiac signals. Sensing circuit 606 includes a cardiac sensing circuit. In a specific example, cardiac signals are sensed using a wearable vest including embedded electrodes configured to sense surface biopotential signals indicative of cardiac activities. The sensed surface biopotential signals are transmitted to implantable medical device via telemetry. In another specific embodiment, ischemia detector 607 detects the ischemic events from one or more wireless electrocardiogram (ECG) signals. Sensing circuit 606 includes a wireless ECG sensing circuit. A wireless ECG is a signal approximating the surface ECG and is acquired without using surface (skin contact) electrodes. An example of a circuit for sensing the wireless ECG is discussed in U.S. patent application Ser. No. 10/795,126, entitled "WIRELESS ECG IN IMPLANTABLE DEVICES," filed on Mar. 5, 2004, assigned to Cardiac Pacemakers, Inc., which is incorporated by reference in its entirety. An example of a wireless ECG-based ischemia detector is discussed in U.S. patent application Ser. No. 11/079,744, entitled "CARDIAC ACTIVATION SEQUENCE MONITORING FOR ISCHEMIA DETECTION," filed on Mar. 14, 2005, assigned to Cardiac Pacemakers, Inc., which is incorporated by reference in its entirety. In another embodiment, ischemia detector 607 detects the ischemic events from one or more electrogram signals. Sensing circuit 606 includes an electrogram sensing circuit. Examples of an electrogram-based ischemia detector are discussed in U.S. Pat. No. 6,108,577, entitled, "METHOD AND APPARATUS FOR DETECTING CHANGES IN ELECTROCARDIOGRAM SIGNALS," and U.S. patent application Ser. No. 09/962,852, entitled "EVOKED RESPONSE SENSING FOR ISCHEMIA DETECTION," filed on Sep. 25, 2001, both assigned to Cardiac Pacemakers, Inc., which are incorporated herein by reference in their entirety.

In another embodiment, ischemia detector 607 detects the ischemic events from one or more impedance signals. Sensing circuit 606 includes an impedance sensing circuit to sense one or more impedance signals each indicative of a cardiac impedance or a transthoracic impedance. Ischemia detector 607 includes an electrical impedance based sensor using a low carrier frequency to detect the ischemic events from an electrical impedance signal. Tissue electrical impedance has been shown to increase significantly during ischemia and decrease significantly after ischemia, as discussed in Dzwonczyk, et al. *IEEE Trans. Biomed. Eng.*, 51(12): 2206-09 (2004). The ischemia detector senses low frequency electrical impedance signal between electrodes interposed in the heart, and detects the ischemia as abrupt changes in impedance (such as abrupt increases in value).

In another embodiment, ischemia detector 607 detects the ischemic events from one or more signals indicative of heart sounds. Sensing circuit 606 includes a heart sound sensing circuit. The heart sound sensing circuit senses the one or more signals indicative of heart sounds using one or more sensors such as accelerometers and/or microphones. Such sensors are included in implantable medical device or incorporated into lead system. Ischemia detector 607 detects the ischemic event by detecting predetermined type heart sounds, predetermined type heart sound components, predetermined type morphological characteristics of heart sounds, or other characteristics of heart sounds indicative of ischemia.

In another embodiment, ischemia detector 607 detects the ischemic events from one or more pressure signals. Sensing circuit 606 includes a pressure sensing circuit coupled to one or more pressure sensors. In a specific embodiment, the pressure sensor is an implantable pressure sensor sensing a signal indicative of an intracardiac or intravascular pressure whose characteristics are indicative of ischemia.

In another embodiment, ischemia detector 607 detects the ischemic event from one or more acceleration signals each indicative of regional cardiac wall motion. Sensing circuit 606 includes a cardiac motion sensing circuit coupled to one or more accelerometers each incorporated into a portion of a lead positioned on or in the heart. The ischemia detector detects ischemia as an abrupt decrease in the amplitude of local cardiac accelerations.

In another embodiment, ischemia detector 607 detects the ischemic event from a heart rate variability (HRV) signal indicative of HRV. Sensing circuit 606 includes an HRV sensing circuit to sense the HRV and produce the HRV signal, which is representative of an HRV parameter. HRV is the beat-to-beat variance in cardiac cycle length over a period of time. The HRV parameter includes any parameter being a measure of the HRV, including any qualitative expression of the beat-to-beat variance in cardiac cycle length over a period of time. In a specific embodiment, the HRV parameter includes the ratio of Low-Frequency (LF) HRV to High-Frequency (HF) HRV (LF/HF ratio). The LF HRV includes components of the HRV having frequencies between about 0.04 Hz and 0.15 Hz. The HF HRV includes components of the HRV having frequencies between about 0.15 Hz and 0.40 Hz. The ischemia detector detects ischemia when the LF/HF ratio exceeds a predetermined threshold. An example of an LF/HF ratio-based ischemia detector is discussed in U.S. patent application Ser. No. 10/669,168, entitled "METHOD FOR ISCHEMIA DETECTION BY IMPLANTABLE CARDIAC DEVICE," filed on Sep. 23, 2003, assigned to Cardiac Pacemakers, Inc., which is incorporated by reference in its entirety.

Control circuit 610 includes a pacing mode switch 617, a pacing mode controller 618, a cardiac protection sequence initiator 619, and a cardiac protection timer 620. Control circuit 610 allows the device to control the delivery of the cardiac protection therapy (pacing and neural stimulation) as well as other pacing therapies. This allows the function of cardiac protection pacing to be included in an implantable medical device that delivers pacing therapies on a long-term basis, such as for treatment of bradycardia and heart failure. In various embodiments, cardiac protection pacing therapy includes a temporary pacing therapy delivered for one or more brief periods in response to the detection of each ischemia event, and the implantable medical device also delivers a chronic pacing therapy such as a bradycardia pacing therapy, or CRT. In other embodiments, the cardiac protection pacing therapy is the only pacing therapy delivered, or the cardiac protection pacing therapy is the only pacing therapy programmed to be delivered for at least a certain period of time.

Each pacing therapy is delivered by delivering pacing pulses in accordance with a predetermined pacing mode. Pacing mode switch 617 switches the pacing mode from a chronic pacing mode to a temporary pacing mode when a cardiac protection pacing sequence is initiated and to switch the pacing mode from the temporary pacing mode to the chronic pacing mode when the cardiac protection pacing sequence is completed. Pacing mode controller 618 controls the delivery of the pacing pulses from pulse output circuit 608 according to the pacing mode as selected by pacing mode switch 617. The temporary pacing mode refers to the pacing mode used in a cardiac protection pacing therapy, which is a temporary pacing therapy. The chronic pacing mode refers to the pacing mode used in a chronic pacing therapy such as a bradycardia pacing therapy, or CRT. In one embodiment, the temporary pacing mode is substantially different from the chronic pacing mode, such that the cardiac protection pacing therapy changes the distribution of stress in the myocardium, thereby triggering the intrinsic myocardial protective mechanism against ischemic damage to the myocardial tissue.

Cardiac protection sequence initiator 619 initiates one or more cardiac protection pacing sequences and neural stimulation sequences in response to the detection of each ischemic event. In one embodiment, cardiac protection sequence initiator 619 also initiates one or more cardiac protection sequences in response to one or more commands issued by the user through external system. For example, following a diagnosis of vulnerable plaque indicative of a high risk for MI, a physician applies a preconditioning therapy by starting a cardiac protection sequence by issuing such a command. Cardiac protection timer 620 times the one or more cardiac protection sequences including the alternating stimulating and non-stimulating periods.

In one embodiment, the one or more cardiac protection sequences initiated in response to the detection of each ischemic event include at least one postconditioning sequence and at least one prophylactic preconditioning sequences. Postconditioning sequence initiator 621 initiates the postconditioning sequence in response to the detection of an ischemic event. In one embodiment, postconditioning sequence initiator 621 initiates the postconditioning sequence when the end of the ischemic event is detected. In one embodiment, the end of the ischemic event is detected when the ischemic event is no longer detected by ischemia detector. In one embodiment, postconditioning sequence initiator 621 initiates the postconditioning pacing sequence when a post-ischemia time interval expires. The post-ischemia time interval starts when the end of the ischemic event is detected and is up to approximately 10 minutes, with approximately 30 seconds being a specific example. In one embodiment, the post-ischemia time interval is chosen such that the postconditioning sequence is initiated after the reperfusion phase following the ischemic event has started. In another embodiment, postconditioning sequence initiator 621 initiates the postconditioning sequence in response to one or more postconditioning commands issued by the user.

In one embodiment, preconditioning sequence initiator 622 initiates the prophylactic preconditioning sequences after the end of the ischemic event is detected and the postconditioning sequence is completed. In one embodiment, preconditioning sequence initiator 622 initiates the prophylactic preconditioning pacing sequences on a periodic basis using a predetermined period such as, according to various embodiments, periods in a range of approximately 24 hours to 72 hours. In another embodiment, preconditioning sequence initiator 622 initiates the prophylactic preconditioning pacing sequences according to a programmed preconditioning schedule. In another embodiment, preconditioning sequence initiator 622 initiates the prophylactic preconditioning pacing sequences in response to one or more preconditioning commands issued by the user. Various embodiments use sensor input (e.g. activity or respiration sensor) to determine a desired time to initiate the sequence.

Postconditioning timer 623 times the postconditioning sequence including alternating postconditioning stimulation and non-stimulation periods. The postconditioning pacing periods each have a postconditioning pacing duration during which a plurality of pacing pulses is delivered. The postconditioning non-pacing periods each have a postconditioning non-pacing duration during which no pacing pulse is delivered. Preconditioning timer 624 times the prophylactic preconditioning sequences including alternating preconditioning stimulation and non-stimulation periods. The preconditioning periods each have a preconditioning stimulation duration during which pacing pulses and neural stimulation is delivered. The pacing and neural stimulation can be delivered simultaneously or sequentially.

In one embodiment, control circuit 610 detects an arrhythmia and suspends the one or more cardiac protection pacing sequences in response to the detection of the arrhythmia. Control circuit includes an arrhythmia detector to detect one or more predetermined types of arrhythmia. In one embodiment, cardiac protection sequence initiator cancels, holds, or otherwise adjusts the timing of the initiation of a cardiac protection sequence in response to a detection of arrhythmia. In one embodiment, cardiac protection timer terminates or suspends a cardiac protection pacing sequence in response to the detection of an arrhythmia that occurs during the cardiac protection sequence. In a specific embodiment, postconditioning sequence initiator cancels the initiation of a postconditioning sequence in response to the detection of arrhythmia. In a specific embodiment, preconditioning sequence initiator holds the initiation of a prophylactic preconditioning sequence in response to the detection of arrhythmia unit the arrhythmia is no longer detected. In one embodiment, cardiac protection timer terminates or suspends a cardiac protection sequence in response to the detection of an arrhythmia that occurs during the cardiac protection sequence.

Figure 7:
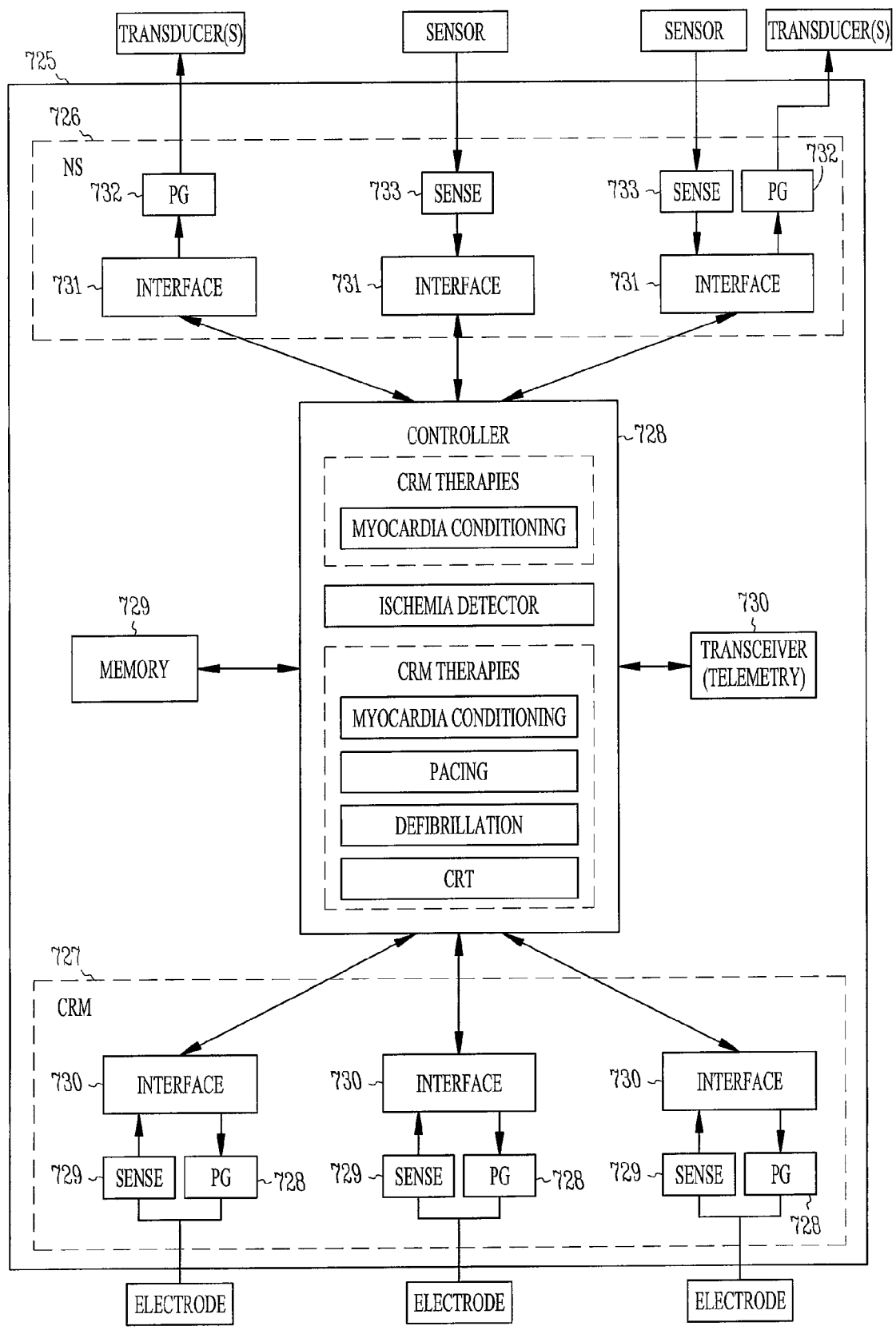
FIG. 7 illustrates an implantable medical device (IMD) having a neural stimulation (NS) component and cardiac rhythm management (CRM) component, according to various embodiments of the present subject matter.

FIG. 7 illustrates an implantable medical device (IMD) 725 having a neural stimulation (NS) component 726 and cardiac rhythm management (CRM) component 727, according to various embodiments of the present subject matter. The illustrated device includes a controller 728 and memory 729. According to various embodiments, the controller includes hardware, software, or a combination of hardware and software to perform the neural stimulation and CRM functions. For example, the programmed therapy applications discussed in this disclosure are capable of being stored as computer-readable instructions embodied in memory and executed by a processor. According to various embodiments, the controller includes a processor to execute instructions embedded in memory to perform the neural stimulation and CRM functions. Examples of CRM functions include bradycardia pacing, antitachycardia therapies such as antitachycardia pacing and defibrillation, and CRT. The controller also executes instructions to detect ischemia. The illustrated device further includes a transceiver 730 and associated circuitry for use to communicate with a programmer or another external or internal device. Various embodiments include a telemetry coil.

The CRM therapy section 727 includes components, under the control of the controller, to stimulate a heart and/or sense cardiac signals using one or more electrodes. The CRM therapy section includes a pulse generator 728 for use to provide an electrical signal through an electrode to stimulate a heart, and further includes sense circuitry 729 to detect and process sensed cardiac signals. An interface 730 is generally illustrated for use to communicate between the controller 728 and the pulse generator 728 and sense circuitry 729. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 726 includes components, under the control of the controller, to stimulate a neural stimulation target and/or sense parameters associated with nerve activity or surrogates of nerve activity such as blood pressure and respiration. Three interfaces 731 are illustrated for use to provide neural stimulation. However, the present subject matter is not limited to a particular number interfaces, or to any particular stimulating or sensing functions. Pulse generators 732 are used to provide electrical pulses to transducer or transducers for use to stimulate a neural stimulation target. According to various embodiments, the pulse generator includes circuitry to set, and in some embodiments change, the amplitude of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. Sense circuits 733 are used to detect and process signals from a sensor, such as a sensor of nerve activity, blood pressure, respiration, and the like. The interfaces 731 are generally illustrated for use to communicate between the controller 728 and the pulse generator 732 and sense circuitry 733. Each interface, for example, may be used to control a separate lead. Various embodiments of the NS therapy section only include a pulse generator to stimulate neural targets such a vagus nerve.

Figure 8:
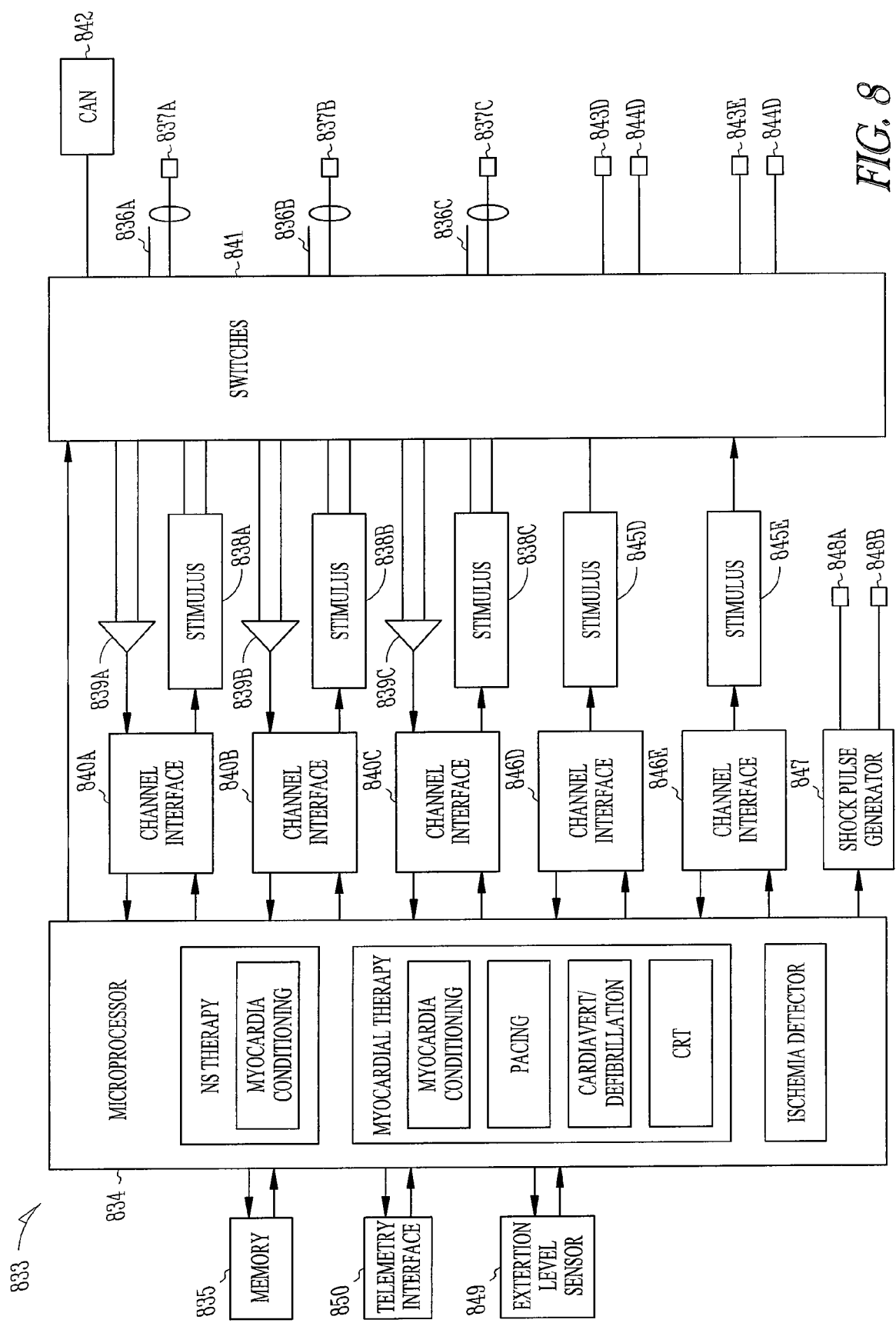
FIG. 8 shows a system diagram of an embodiment of a microprocessor-based implantable device, according to various embodiments.

FIG. 8 shows a system diagram of an embodiment of a microprocessor-based implantable device. The device 833 is equipped with multiple sensing and pacing channels which may be physically configured to sense and/or pace multiple sites in the atria or the ventricles, and to provide neural stimulation. The illustrated device can be configured for myocardial stimulation (e.g. myocardium conditioning pacing, bradycardia pacing, defibrillation, CRT) and neural stimulation (e.g. myocardium conditioning parasympathetic stimulation). The multiple sensing/pacing channels may be configured, for example, with one atrial and two ventricular sensing/pacing channels for delivering biventricular resynchronization therapy, with the atrial sensing/pacing channel used to deliver the biventricular resynchronization therapy in an atrial tracking mode as well as to pace the atria if required. The controller 834 of the device is a microprocessor which communicates with memory 835 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor.

Shown in FIG. 8, by way of example, are three sensing and pacing channels, such as can be used to provide myocardial stimulation/pacing, designated "A" through "C" comprising bipolar leads with ring, or proximal, electrodes 836A-C and distal, or tip, electrodes 837A-C, pulse generators 838A-C, sensing amplifiers 839A-C, and channel interfaces 840A-C. Each channel thus includes a pacing channel made up of the pulse generator connected to the electrode and a sensing channel made up of the sense amplifier connected to the electrode. The channel interfaces 840A-C communicate bidirectionally with the microprocessor 834, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively. The pacing algorithms also include the appropriate preconditioning and postconditioning pacing algorithms.

The electrodes of each bipolar lead are connected via conductors within the lead to a switching network 841 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring, or proximal, and tip, or distal, electrodes of a lead or in a unipolar mode using only one of the electrodes of the lead with the device housing or can 842 serving as a ground electrode.

Also shown in FIG. 8, by way of example, are nerve stimulation channels designated "D" and "E." Neural stimulation channels are incorporated into the device. These channels can be used to deliver neural stimulation to elicit a parasympathetic response as part of a cardioprotective therapy. The illustrated channels include leads with electrodes 843D and 844D and electrodes 843E and 844E, a pulse generator 845D and 845E, and a channel interface 846D and 846E. The illustrated bipolar arrangement is intended as a non-exclusive example. Other neural stimulation electrode arrangements are within the scope of the present subject matter. Other embodiments may use unipolar leads in which case the neural stimulation pulses are referenced to the can or another electrode. The pulse generator for each channel outputs a train of neural stimulation pulses which may be varied by the controller as to amplitude, frequency, duty-cycle, pulse duration, and wave morphology, for example. A shock pulse generator 847 is also interfaced to the controller for delivering a defibrillation shock via a pair of shock electrodes 848A and 848B to the atria or ventricles upon detection of a shockable tachyarrhythmia.

The illustrated controller includes a module for controlling neural stimulation (NS) therapy and module for controlling myocardial therapy. As illustrated, the NS therapy module includes a module for performing myocardial conditioning (e.g. vagal nerve stimulation or stimulation of a cardiac fat pad). Also as illustrated, the myocardial therapy module includes a module for controlling myocardial conditioning pacing, a module for controlling bradycardia pacing therapies, a module for controlling defibrillation therapies, and a module for controlling CRT. The illustrated controller also includes a module to detect ischemia, used to trigger myocardial conditioning, including both parasympathetic stimulation and myocardial pacing.

The controller controls the overall operation of the device in accordance with programmed instructions stored in memory, including controlling the delivery of paces via the pacing channels, interpreting sense signals received from the sensing channels, and implementing timers for defining escape intervals and sensory refractory periods. The controller is capable of operating the device in a number of programmed pacing modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity such that a pacing pulse is delivered to a heart chamber during a cardiac cycle only after expiration of a defined escape interval during which no intrinsic beat by the chamber is detected. Escape intervals for ventricular pacing can be restarted by ventricular or atrial events, the latter allowing the pacing to track intrinsic atrial beats. CRT is most conveniently delivered in conjunction with a bradycardia pacing mode where, for example, multiple excitatory stimulation pulses are delivered to multiple sites during a cardiac cycle in order to both pace the heart in accordance with a bradycardia mode and provide pre-excitation of selected sites. An exertion level sensor 849 (e.g., an accelerometer, a minute ventilation sensor, or other sensor that measures a parameter related to metabolic demand) enables the controller to adapt the pacing rate in accordance with changes in the patient's physical activity and can enable the controller to modulate the delivery of neural stimulation and/or cardiac pacing. A telemetry interface 850 is also provided which enables the controller to communicate with an external programmer or remote monitor.

System Examples

Figure 9:
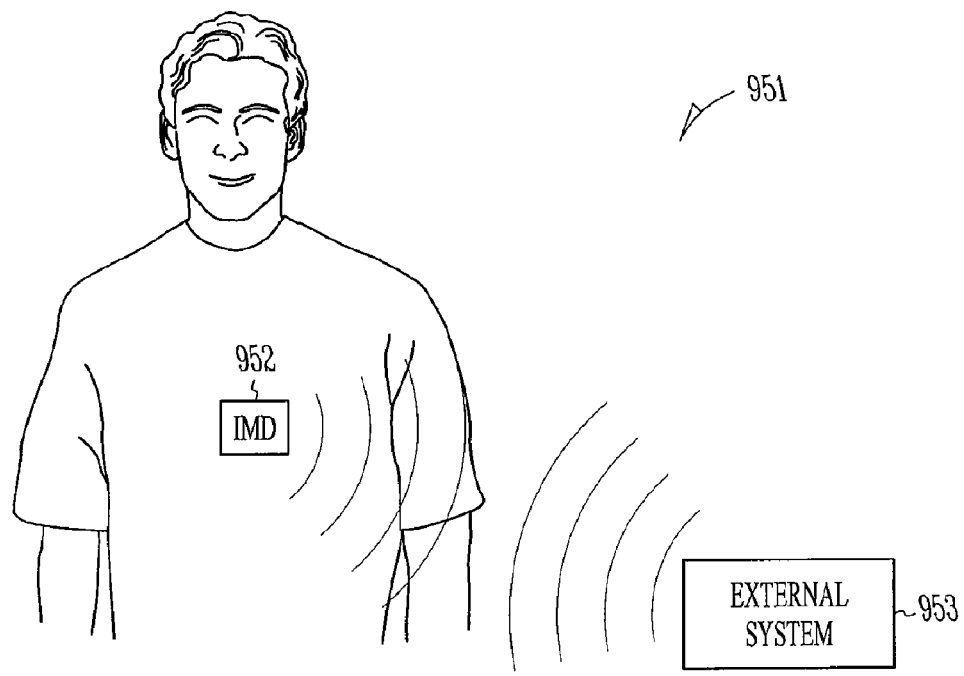
FIG. 9 illustrates a system including an implantable medical device (IMD) and an external system or device, according to various embodiments of the present subject matter.

FIG. 9 illustrates a system 951 including an implantable medical device (IMD) 952 and an external system or device 953, according to various embodiments of the present subject matter. Various embodiments of the IMD 952 include a combination of NS and CRM functions. The IMD may also deliver biological agents and pharmaceutical agents. The external system 953 and the IMD 952 are capable of wirelessly communicating data and instructions. In various embodiments, for example, the external systems 953 and IMD 952 use telemetry coils to wirelessly communicate data and instructions. Thus, the programmer can be used to adjust the programmed therapy provided by the IMD 952, and the IMD can report device data (such as battery and lead resistance) and therapy data (such as sense and stimulation data) to the programmer using radio telemetry, for example. According to various embodiments, the IMD 952 stimulates a parasympathetic target to provide a myocardium conditioning therapy, and paces myocardium as part of the myocardium conditioning therapy.

In one embodiment, in addition to the cardiac protection pacing therapy, the IMD 952 also delivers one or more other cardiac pacing therapies, such a bradycardia pacing therapy, and CRT. If another pacing therapy is being delivered when a cardiac protection pacing sequence is to be initiated, that pacing therapy is temporarily suspended to allow the delivery of the cardiac protection pacing therapy and resumed upon completion of the cardiac protection pacing sequence.

External system 953 allows a user such as a physician or other caregiver or a patient to control the operation of IMD 952 and obtain information acquired by the IMD 952. In one embodiment, external system 953 includes a programmer communicating with the IMD 952 bi-directionally via a telemetry link. In another embodiment, the external system 953 is a patient management system including an external device communicating with a remote device through a telecommunication network. The external device is within the vicinity of the IMD 952 and communicates with IMD bi-directionally via a telemetry link. The remote device allows the user to monitor and treat a patient from a distant location. The patient monitoring system is further discussed below.

The telemetry link provides for data transmission from implantable medical device to external system. This includes, for example, transmitting real-time physiological data acquired by IMD, extracting physiological data acquired by and stored in IMD, extracting therapy history data stored in implantable medical device, and extracting data indicating an operational status of IMD (e.g., battery status and lead impedance). Telemetry link also provides for data transmission from external system to IMD. This includes, for example, programming IMD to acquire physiological data, programming IMD to perform at least one self-diagnostic test (such as for a device operational status), and programming IMD to deliver at least one therapy.

Figure 10:
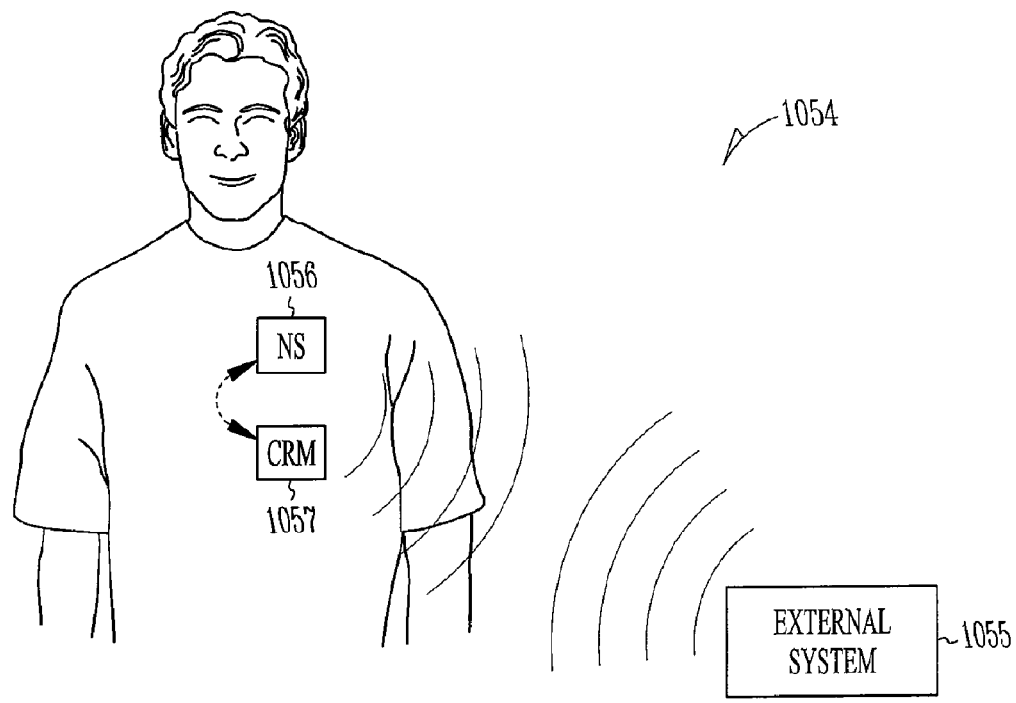
FIG. 10 illustrates a system including an external device, an implantable neural stimulator (NS) device and an implantable cardiac rhythm management (CRM) device, according to various embodiments of the present subject matter.

FIG. 10 illustrates a system 1054 including an external device 1055, an implantable neural stimulator (NS) device 1056 and an implantable cardiac rhythm management (CRM) device 1057, according to various embodiments of the present subject matter. Various aspects involve a method for communicating between an NS device 1056 and a CRM device 1057 or other cardiac stimulator. The NS device 1056 delivers parasympathetic stimulation for a myocardium conditioning therapy, and the CRM device 1057 delivers myocardium pacing therapy for the myocardium conditioning therapy. In various embodiments, this communication allows one of the devices 1056 or 1057 to deliver more appropriate therapy (i.e. more appropriate NS therapy or CRM therapy) based on data received from the other device. Some embodiments provide on-demand communications. In various embodiments, this communication allows each of the devices to deliver more appropriate therapy (i.e. more appropriate NS therapy and CRM therapy) based on data received from the other device. The illustrated NS device and the CRM device are capable of wirelessly communicating with each other, and the external system is capable of wirelessly communicating with at least one of the NS and the CRM devices. For example, various embodiments use telemetry coils to wirelessly communicate data and instructions to each other. In other embodiments, communication of data and/or energy is by ultrasonic means. Rather than providing wireless communication between the NS and CRM devices, various embodiments provide a communication cable or wire, such as an intravenously-fed lead, for use to communicate between the NS device and the CRM device.

Figure 11:
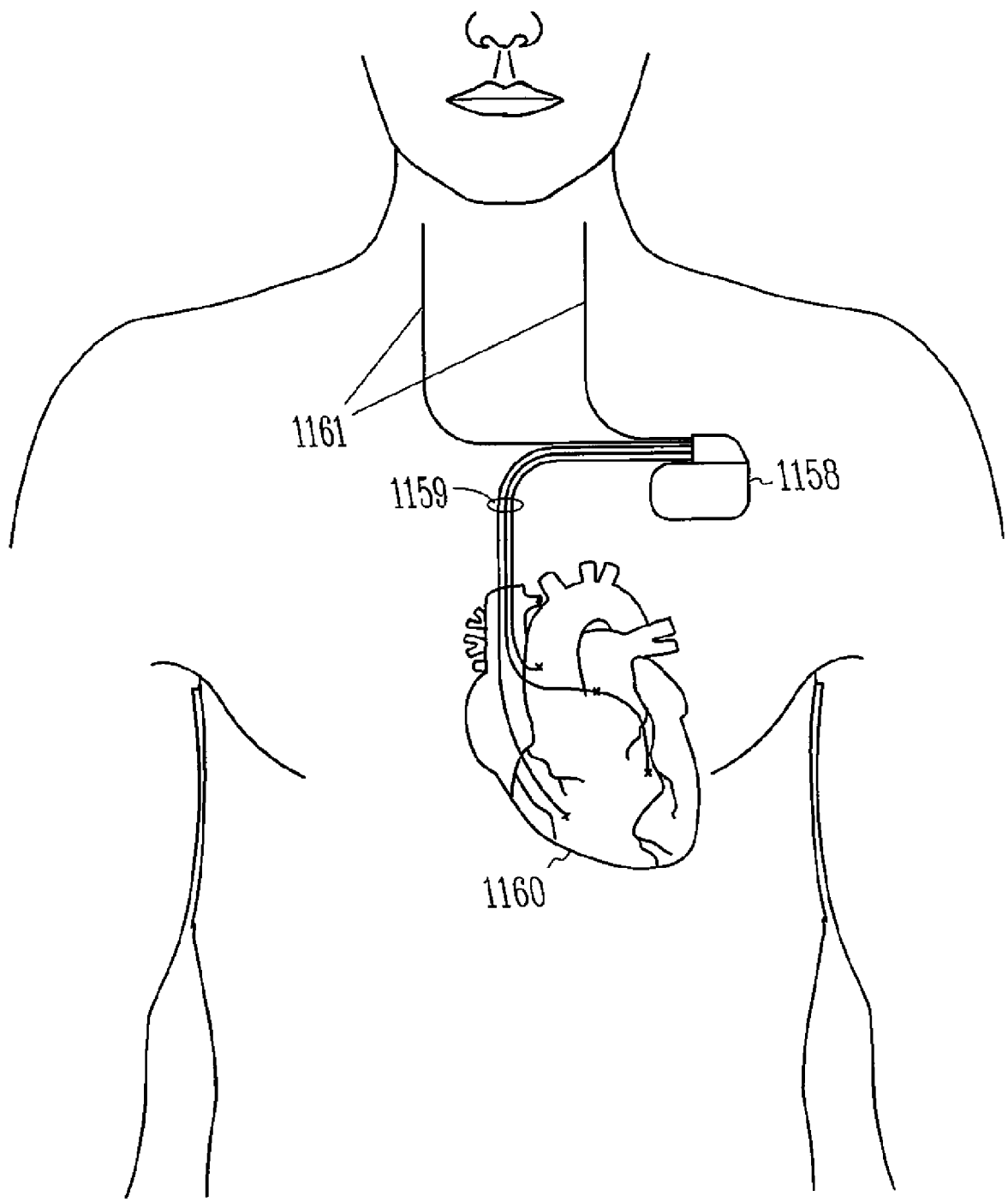
FIG. 11 illustrates an IND placed subcutaneously or submuscularly in a patient's chest with lead(s) positioned to provide a CRM therapy to a heart, and with lead(s) positioned to stimulate a vagus nerve, by way of example and not by way of limitation, according to various embodiments.

FIG. 11 illustrates an IMD 1158 placed subcutaneously or submuscularly in a patient's chest with lead(s) 1159 positioned to provide a CRM therapy to a heart 1160, and with lead(s) 1161 positioned to stimulate a vagus nerve, by way of example and not by way of limitation. The leads 1159 can be used to delivery the myocardium pacing to condition myocardium. According to various embodiments, the leads 1159 are positioned in or proximate to the heart to provide a desired cardiac pacing therapy. In some embodiments, the lead(s) 1159 are positioned in or proximate to the heart to provide a desired defibrillation therapy. In some embodiments, the lead(s) 1159 are positioned in or proximate to the heart to provide a desired CRT therapy. Some embodiments place the leads in positions with respect to the heart that enable the lead(s) to deliver the combinations of at least two of the pacing, defibrillation and CRT therapies. According to various embodiments, neural stimulation lead(s) 1161 are subcutaneously tunneled to a neural target, and can have a nerve cuff electrode to stimulate the neural target. Some lead embodiments are intravascularly fed into a vessel proximate to the neural target, and use transducer(s) within the vessel to transvascularly stimulate the neural target. For example, some embodiments stimulate the vagus using electrode(s) positioned within the internal jugular vein.

Figure 12:
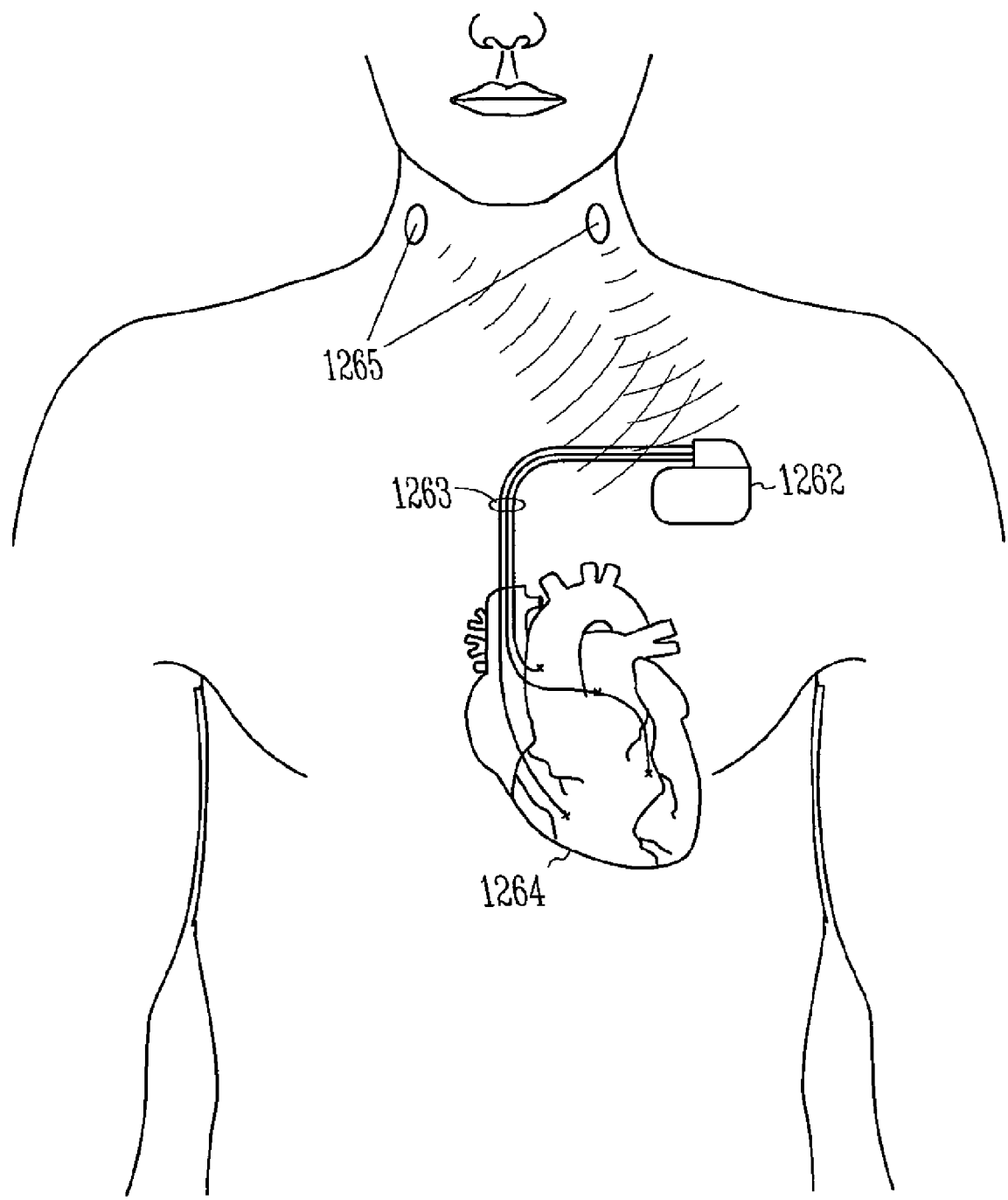
FIG. 12 illustrates an IMD with lead(s) positioned to provide a CRM therapy to a heart, and with satellite transducers positioned to stimulate at least one parasympathetic neural target as part of a myocardium conditioning therapy, according to various embodiments.

FIG. 12 illustrates an IMD 1262 with lead(s) 1263 positioned to provide a CRM therapy to a heart 1264, and with satellite transducers 1265 positioned to stimulate at least one parasympathetic neural target as part of a myocardium conditioning therapy. The satellite transducers are connected to the IMD, which functions as the planet for the satellites, via a wireless link. Stimulation and communication can be performed through the wireless link. Examples of wireless links include RF links and ultrasound links. Although not illustrated, some embodiments perform myocardial stimulation using wireless links. Examples of satellite transducers include subcutaneous transducers, nerve cuff transducers and intravascular transducers.

Figure 13:
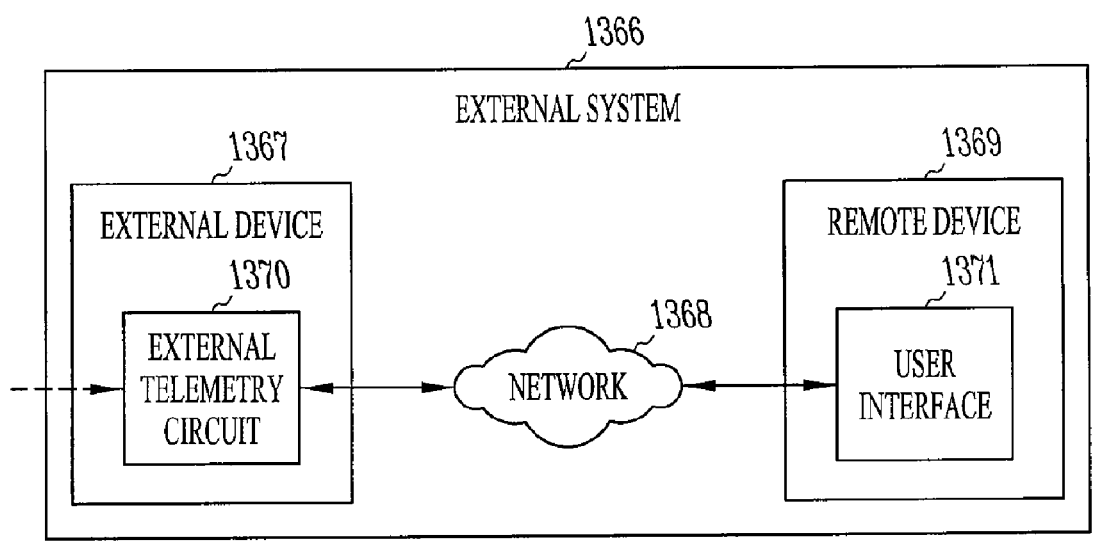
FIG. 13 is a block diagram illustrating an embodiment of an external system.

The external system illustrated in FIGS. 9-10 includes a programmer, in some embodiments, and includes a patient management system in other embodiments. FIG. 13 is a block diagram illustrating an embodiment of an external system 1366. As illustrated, external system 1366 is a patient management system including an external device 1367, a telecommunication network 1368, and a remote device 1369. External device 1366 is placed within the vicinity of an IMD and includes external telemetry system 1370 to communicate with the MD. Remote device(s) 1369 is in one or more remote locations and communicates with external device 1367 through network 1368, thus allowing a physician or other caregiver to monitor and treat a patient from a distant location and/or allowing access to various treatment resources from the one or more remote locations. In one embodiment, remote device 1369 includes a user interface 1371. This allows the user to initiate and/or adjust the cardiac protection pacing therapy.

One of ordinary skill in the art will understand that, the modules and other circuitry shown and described herein can be implemented using software, hardware, and combinations of software and hardware. As such, the term module is intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. A system, comprising:
   means for providing cardioprotective therapy to treat heart disease through modulation of an Akt-mediated pathway,
   wherein the means for providing cardioprotective therapy to treat heart disease includes both means for providing cardioprotective myocardial pacing therapy to modulate the Akt-mediated pathway, and means for providing cardioprotective neural stimulation therapy to elicit a parasympathetic response to modulate the Akt-mediated pathway,
   wherein the means for providing cardioprotective myocardial pacing therapy includes means for delivering a programmed myocardial pacing sequence to modulate the Akt-mediated pathway, wherein the means for delivering the programmed myocardial pacing sequence includes means for initiating and timing a sequence of myocardial pacing pulses, wherein the programmed myocardial pacing sequence includes alternating pacing periods with a programmed pacing duration and non-pacing periods with a programmed non-pacing duration, wherein each pacing period in the programmed myocardial pacing sequence includes the timed sequence of myocardial pacing pulses delivered to a myocardium for the duration of each of the pacing periods and not delivering myocardial pacing pulses during each of the non-pacing periods.

2. The system of claim 1, wherein the means for providing cardioprotective therapy includes means for providing therapeutic postconditioning therapy after an ischemic event.

3. The system of claim 1, wherein the means for providing cardioprotective therapy includes means for providing prophylactic preconditioning therapy in anticipation of an ischemic event.

4. The system of claim 1, further comprising means for detecting an ischemia event, and means for providing the cardioprotective therapy in response to the detected ischemia event.

5. The system of claim 1, wherein the means for delivering the programmed myocardial pacing sequence includes:
   means for initiating the pacing period;
   means for, upon initiating the pacing period, delivering the timed sequence of myocardial pacing pulses for the programmed pacing duration; and
   means for, upon completion of the pacing duration, initiating a subsequent pacing period after the programmed non-pacing duration.

6. The system of claim 1, wherein the means for providing cardioprotective pacing therapy includes means for integrating the cardioprotective neural stimulation therapy with the cardioprotective myocardial pacing therapy to provide the cardioprotective therapy.

7. The system of claim 1, wherein the means for providing cardioprotective therapy includes a neural stimulator and a pulse generator integrated into a single pulse generator circuit to provide the cardioprotective myocardial pacing therapy and the cardioprotective neural stimulation therapy.

8. The system of claim 1, wherein:
   the means for providing cardioprotective therapy includes a neural stimulator to provide the cardioprotective neural stimulation therapy and a pulse generator to provide the cardioprotective myocardial pacing therapy; and
   the neural stimulator is distinct from the pulse generator.

9. The system of claim 1, further comprising:
   means for detecting an ischemia event;
   means for automatically responding the to the detected ischemia event by providing a postconditioning cardioprotective therapy for the detected ischemia event, followed by a preconditioning cardioprotective therapy in anticipation of a subsequent ischemic event.

10. The system of claim 1, wherein the means for providing cardioprotective neural stimulation therapy to elicit a parasympathetic response includes means for transvascularly stimulating a vagus nerve from an internal jugular vein to elicit the parasympathetic response.

11. The system of claim 1, wherein the means for providing cardioprotective neural stimulation therapy to elicit a parasympathetic response includes means for stimulating a vagus nerve using a nerve cuff to elicit the parasympathetic response.

12. The system of claim 1, wherein the sequence of alternating pacing and non-pacing periods includes a regular interval between pacing periods.

13. The system of claim 1, wherein the means for providing cardioprotective neural stimulation therapy includes means for inhibiting sympathetic nerve traffic.

14. The system of claim 1, wherein the means for providing cardioprotective neural stimulation therapy includes means for stimulating parasympathetic nerve traffic.

15. The system of claim 1, wherein the system includes:
   means for providing at least two pacing modes for pacing myocardial tissue, wherein one of the at least two pacing modes includes the cardioprotective myocardial pacing therapy; and
   means for interrupting another one of the at least two pacing modes to deliver the cardioprotective myocardial pacing therapy.

16. A method, comprising:
   providing cardioprotective therapy to treat heart disease through modulation of an Akt-mediated pathway,
   wherein providing cardioprotective therapy to treat heart disease includes both providing cardioprotective myocardial pacing therapy to modulate the Akt-mediated pathway, and providing cardioprotective neural stimulation therapy to elicit a parasympathetic response to modulate the Akt-mediate pathway,
   wherein providing cardioprotective myocardial pacing therapy includes delivering a programmed myocardial pacing sequence to modulate the Akt-mediated pathway,
   wherein delivering the programmed myocardial pacing sequence includes initiating and timing a sequence of myocardial pacing pulses, wherein the programmed myocardial pacing sequence includes alternating pacing periods with a programmed pacing duration and non-pacing periods with a programmed non-pacing duration, wherein each pacing period in the programmed myocardial pacing sequence includes the timed sequence of myocardial pacing pulses delivered to a myocardium for the duration of each of the pacing periods in the programmed myocardial pacing sequence and not delivering myocardial pacing pulses during each of the a non-pacing periods in the programmed myocardial pacing sequence.

17. The method of claim 16, wherein providing cardioprotective therapy includes providing therapeutic postconditioning therapy after an ischemic event.

18. The method of claim 16, wherein providing cardioprotective therapy includes providing prophylactic preconditioning therapy in anticipation of an ischemic event.

19. The method of claim 16, further comprising detecting an ischemia event, and providing the cardioprotective therapy in response to the detected ischemia event.

20. The method of claim 16, wherein providing cardioprotective neural stimulation therapy includes providing vagus nerve stimulation.

21. The method of claim 16, wherein providing cardioprotective neural stimulation therapy includes providing neural stimulation to a vagus nerve branch.

22. The method of claim 16, wherein providing cardioprotective neural stimulation therapy includes providing neural stimulation to a cardiac fat pad.

23. The method of claim 16, wherein providing cardioprotective neural stimulation therapy includes providing neural stimulation therapy to stimulate parasympathetic nerve traffic.

24. The method of claim 16, wherein providing cardioprotective neural stimulation therapy includes providing neural stimulation therapy to inhibit sympathetic nerve traffic.

25. The method of claim 16, wherein providing cardioprotective transvascularly stimulating a vagus nerve from an internal jugular vein.

26. The method of claim 16, wherein delivering the programmed myocardial pacing sequence includes:
   initiating the pacing period;
   upon initiating the pacing period, delivering the timed sequence of myocardial pacing pulses for the programmed pacing duration; and
   upon completion of the pacing duration, initiating a subsequent pacing period after the programmed non-pacing duration.

27. The method of claim 16, wherein providing cardioprotective pacing therapy includes integrating the cardioprotective neural stimulation therapy with the cardioprotective myocardial pacing therapy to provide the cardioprotective neural stimulation only during the pacing periods.

28. The method of claim 16, wherein providing cardioprotective therapy includes integrating the cardioprotective neural stimulation therapy with the cardioprotective myocardial pacing therapy to provide the cardioprotective neural stimulation only during the non-pacing periods.

29. The method of claim 16, further comprising:
   detecting an ischemia event; and
   automatically responding the to the detected ischemia event by providing a postconditioning cardioprotective therapy for the detected ischemia event, followed by a preconditioning cardioprotective therapy in anticipation of a subsequent ischemic event.

30. The method of claim 16, wherein the method includes:
   providing at least two pacing modes for pacing myocardial tissue, wherein one of the at least two pacing modes includes the cardioprotective myocardial pacing therapy; and
   interrupting another one of the at least two pacing modes to deliver the cardioprotective myocardial pacing therapy.

* * * * *

UNITED STATES PATENT AND TRADEMARK OFFICE
CERTIFICATE OF CORRECTION

PATENT NO. : 7,689,286 B2  Page 1 of 1
APPLICATION NO. : 11/381211
DATED : March 30, 2010
INVENTOR(S) : Joseph M. Pastore et al.

It is certified that error appears in the above-identified patent and that said Letters Patent is hereby corrected as shown below:

In column 5, line 59, delete "repurfusing" and insert -- reperfusing --, therefor.

In column 5, line 62, delete "parasympathethic" and insert -- parasympathetic --, therefor.

In column 17, line 32, in Claim 9, after "responding" delete "the".

In column 18, line 21, in Claim 16, after "the" delete "a".

In column 19, line 6, in Claim 29, after "responding" delete "the".

Signed and Sealed this

Eighth Day of June, 2010

David J. Kappos
*Director of the United States Patent and Trademark Office*